United States Patent [19]
Malmborg

[11] Patent Number: 4,927,423

[45] Date of Patent: May 22, 1990

[54] CONNECTOR AND A DISPOSABLE ASSEMBLY UTILIZING SAID CONNECTOR

[75] Inventor: Bengt Malmborg, Helsingborg, Sweden

[73] Assignee: Aktiebolaget Leo, Helsingborg, Sweden

[21] Appl. No.: 193,282

[22] Filed: May 11, 1988

[30] Foreign Application Priority Data

| | | | |
|---|---|---|---|
| Sep. 18, 1986 | [SE] | Sweden | 8603928 |
| Dec. 9, 1986 | [SE] | Sweden | 8605259 |

[51] Int. Cl.[5] .......... A61M 5/00

[52] U.S. Cl. .......... 604/88; 604/283; 604/412

[58] Field of Search .......... 604/82, 87, 88, 89, 604/201, 283, 411–415

[56] References Cited

U.S. PATENT DOCUMENTS

| | | | |
|---|---|---|---|
| 2,724,383 | 11/1955 | Lockhart | 604/88 |
| 2,828,743 | 4/1958 | Ashkenaz et al. | 604/201 |
| 3,150,661 | 9/1964 | Maki . | |
| 3,375,825 | 4/1968 | Keller . | |
| 3,826,260 | 7/1974 | Killinger . | |
| 4,084,588 | 4/1978 | Koenig . | |
| 4,516,967 | 5/1985 | Kopfer . | |
| 4,576,211 | 3/1986 | Valentini et al. | 604/88 |
| 4,581,016 | 4/1986 | Gettig . | |
| 4,581,023 | 4/1986 | Kuntz . | |
| 4,582,207 | 4/1986 | Howard et al. . | |
| 4,607,671 | 8/1986 | Aalto et al. | 604/415 |
| 4,619,651 | 10/1986 | Kopfer et al. | 604/87 |
| 4,675,020 | 6/1987 | McPhee | 604/414 |
| 4,743,229 | 5/1988 | Chu | 604/82 |
| 4,759,756 | 7/1988 | Forman et al. | 604/413 |

FOREIGN PATENT DOCUMENTS

| | | |
|---|---|---|
| 1766152 | 6/1971 | Fed. Rep. of Germany . |
| 8009999 | 5/1979 | France . |
| WO86/05683 | 10/1986 | PCT Int'l Appl. . |
| 2050184A | 7/1981 | United Kingdom . |

*Primary Examiner*—Dalton L. Truluck
*Assistant Examiner*—Denise W. DeFranco
*Attorney, Agent, or Firm*—Pravel, Gambrell, Hewitt, Kimball & Krieger

[57] ABSTRACT

A disposable assembly comprises a drug container (2) having at one end an opening which is surrounded by an outwardly directed flange (7). A connector (1) has a sleeve (13) which is closed (14) at one end and open at its opposite end to receive the flanged end of the drug container as a plunger. Positioning means (18,19) provided within the sleeve and cooperating with the flange define an inserted and a retracted position of said sleeve relative to the flanged end of the drug container. A piercing member (15) provided at the closed end of the sleeve is directed towards the open sleeve end. A connecting member (16) provided at the closed sleeve end is directed opposite to said piercing member (15) and communicating therewith by means of a through passage (17).

11 Claims, 5 Drawing Sheets

A
B
C
D
E
F
27
26
10
10
10
10
10

CONNECTOR AND A DISPOSABLE ASSEMBLY UTILIZING SAID CONNECTOR

The present invention relates generally to the handling of toxic substances and drugs, especially pharmacologically active, hazardous substances.

More particularly, the invention relates to a connector for a container having at one end an opening which is closed by means of a pierceable closure and which is surrounded by an outwardly directed flange, and having a plunger movable within the container and closely engaging the container inner wall, a toxic substance, e.g. a drug component, being enclosed between said plunger and said closure, for mixing with a liquid prior to administration.

The invention also relates to a disposable assembly comprising said container, said connector and, optionally, a container for the liquid, interconnected to form a unit.

Many different types of pharmaceuticals are hazardous and risky to handle. Medical staff exposed to these drugs when preparing mixtures for administration to patients must take many precautions to avoid the risks associated with the handling of the drugs. In view hereof, there is urgent need for devices which reduce the staff's exposure to such drugs and which could simplify their routines to a considerable extent.

Cytostatic drugs as used for the treatment of cancer are one type of drug which requires safe handling. These drugs are often supplied by the manufacturer in the form of a dry powder in a sealed glass vial together with an ampoule containing the solvent, for example water or an aqueous solution, for dissolving the drug. The most important steps which the medical staff must take in order to prepare a drug solution ready for adminiStration, such as injection, to the patient, may be summarised as follows: (1) opening an ampoule containing the solvent and drawing the solvent from the ampoule up into a syringe; (2) carefully emptying the solvent to avoid excess pressure from the syringe into a vessel containing the dry cytostatic agent; (3) drawing the dissolved drug, after a period of dissolution, carefully up into a syringe intended for the administration.

It is recommended that this preparation be carried out in a fume cupboard and a well-aerated room, and also that the work be done by specially trained personnel.

The preparation technique described also involves a risk of contamination, incorrect dosing and, furthermore, a risk that the wrong components are mixed, especially if mixing is effected by untrained staff members.

Many attempts at solving these problems have been made, for example by supplying the syringe and the ampoule connected together by means of a special connector. Examples of such combinations are disclosed in, inter alia, US-A-3,826,260, WO-A1-86/05683 and DE-A-1,766,152.

The combination according to US-A-3,826,260 comprises a syringe containing a solvent, a vial containing a drug, and a connector including a cannula. The syringe is of the type having a neck and a seal, the seal being held in position by a specially designed sleeve of reduced diameter. The vial is of similar construction and has a seal and a specially designed sleeve. The cannula is mounted in a support which is movable from an outer to an inner position on the first-mentioned sleeve. Although this combination is intended for mixing a drug with a solvent, mixing takes place in the vial, not in the syringe. The specially designed sleeve of the syringe and the vial for connection with the cannula support and the connector, respectively, make this combination complicated and fairly long. Furthermore, the combination does not permit connection to an optional means of administration.

WO-A1-86/05683 discloses a device for transferring two components of a drug between two containers and to the patient, respectively. The device comprises a connector having a single or double cannula. Two sleeve-shaped supports can be screwed onto the connector to protect the cannula. Different types of containers are insertable through the supports to a position in which the cannula ends pierce the seals at the container ends. In this manner, the component of one container can be transferred to the component of the other container. The device requires further protective means for the cannula ends in the event that the supports are not attached to the connector. However, also these protective means must be pierceable by the cannula points. When this device is to be used, the supports are interconnected with a connector, whereupon two containers, each with one component, can be interconnected via the cannula by inserting them into the supports in a direction toward one another. After the component of one container has been transferred to the other container, the empty container is removed and replaced by a container having a retractable plunger, and the two components which are now mixed, are transferred to the latter container prior to administration.

DE-A1-1,766,152 discloses a device for converting a single-compartment syringe into a two-compartment syringe. The device comprises two sleeves, each having an open end and a closed end. Extending through the sealed end of one sleeve is a double-pointed cannula, and this sealed end also has an external thread for threaded engagement with an internal thread in the open end of the other sleeve. Each sleeve has a container with a seal immediately adjacent each cannula point. When the device is to be used, the sleeves are screwed together and the cannula with its two points pierces the seals of the containers. The components in the containers can now be mixed by retracting a plunger in one of the containers. Finally, the sleeves are unscrewed from one another to provide a syringe ready for administration of the mixed drug.

The object of the present invention is to provide a connector which is intended for containers with flanged ends and which satisfies the requirements stipulated for the handling of poisonous drugs, viz. that the staff handling the drug must not be exposed thereto during any phase of the handling, and that no contamination must occur. In addition, the connector should be simple, inexpensive and comprise but few parts, such that it can form part of a disposable assembly. Furthermore, the connector must be connectible to different means of administration.

This object is achieved, according to the present invention, in that the connector is in the form of a sleeve which is closed at one end, which is open at its opposite end to receive the flanged container end as a plunger, and which has internal positioning means cooperating with the flange and adapted to define an inserted and an extracted position of said sleeve relative to the flanged end of the container; a piercing member provided at the sealed end of the sleeve and directed towards the open sleeve end and adapted to pierce the closure of the container upon displacement of the sleeve from the retracted to the inserted position; and a connecting member provided at the closed sleeve end and directed opposite to said piercing member and connected therewith by means of a through passage, for connection of the substance or drug container first to a liquid container for sucking up liquid in said substance or drug container by retraction of the plunger therein, and then to a means for administration of the substance/liquid mixture.

The connector thus is a single element which cooperates directly with the outwardly directed flange on the container. Because of the positioning means according to the invention, the container can be safely moved between the two positions relative to the sleeve whereby, in particular, resealing of the container can be effected during the mixing of the drug component and the liquid by displacing the sleeve from the inserted to the extracted position in which the piercing member is outside the closure which thus can reseal the opening in the container end.

The positioning means may be in the form of at least one inwardly directed bead on the inner side of the sleeve. In an especially advantageous embodiment, the connecting member also constitutes a piercing member for a pierceable closure of the liquid container. In this embodiment, the connector preferably has a sleeve extension extending in the same direction as the connecting member, for guiding the liquid container toward the connecting member. Internal positioning means may also be arranged in the sleeve extension to define an inserted and a retracted position of the extension relative to the liquid container.

Connection to the means of administration is simplified considerably if the extension is designed for breakaway removal from the sleeve.

The invention comprises not only the connector, but also a combination of the connector and the said drug container, as well as a combination of the connector, the said drug container and the said liquid container.

The invention will be described in more detail below, reference being had to the accompanying drawings.

Figure 1:
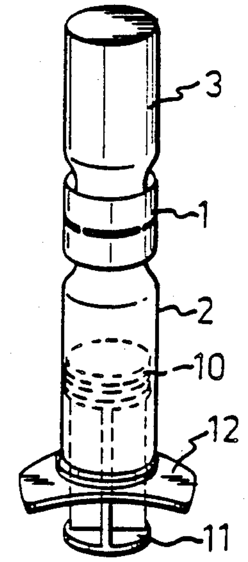
FIG. 1 illustrates a preferred embodiment of the disposable assembly according to the invention, comprising a drug container, a connector, and a liquid container.
Figure 2:
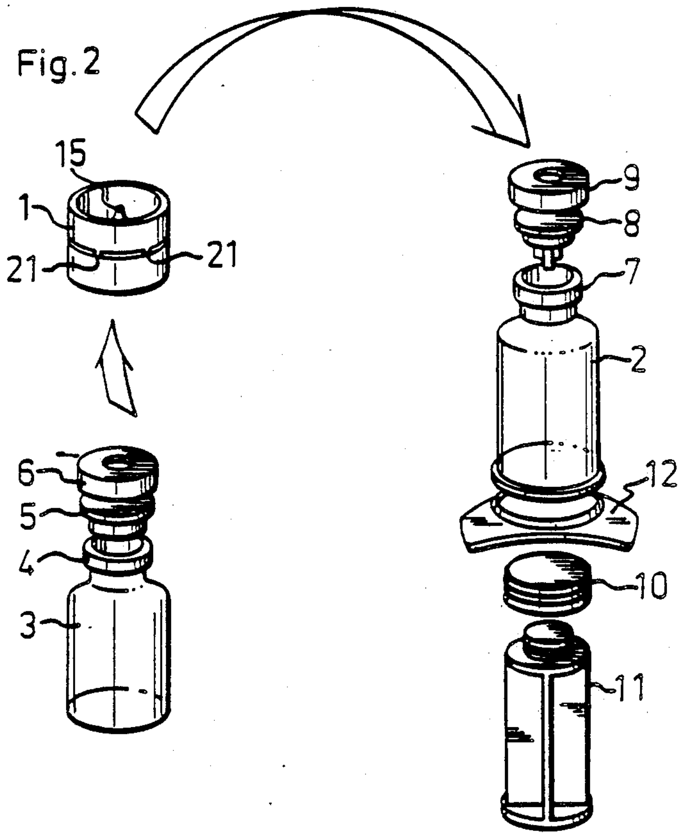
FIG. 2 is an exploded perspective view of the parts comprised by the disposable assembly according to FIG. 1.

The disposable assembly shown in FIGS. 1 and 2 comprises a connector 1, a container 2 for a drug component and a liquid container 3. The container 3 is a conventional vial having a neck and a flange 4 around the neck opening, a closure 5 in the form of, for example, a rubber stopper, and a cap 6 having a central hole and intended to keep the closure 5 in position in the neck opening by engaging the flange 4. Also the container 2 has a neck provided with a flange 7, a closure 8 and a cap 9. A plunger 10 is displaceable within the container 2 by means of a plunger rod 11, insertion of the plunger 10 being simplified by a finger grip 12 on the container 2. The plunger 10 and the plunger rod 11 are disconnectible from one another by means of a threaded connection.

In manufacturing the disposable assembly according to FIG. 1, a drug component is first introduced into the container 2 with the plunger 10 partly inserted therein, whereupon the container 2 is closed by means of the closure 8 which may be a stopper suitable for freeze-drying and is secured in position by means of the cap 9. The liquid to be admixed to the drug component of the container 2 is filled into the container 3 which then is closed by means of the closure 5 and the cap 6. After that, the containers 2 and 3 are interconnected by means of the connector 1, the container 2 and also the container 3 being fixed in a retracted position relative to the connector 1 by cooperation between the flange 4, 7 and internal positioning means in the connector 1.

Figure 3:
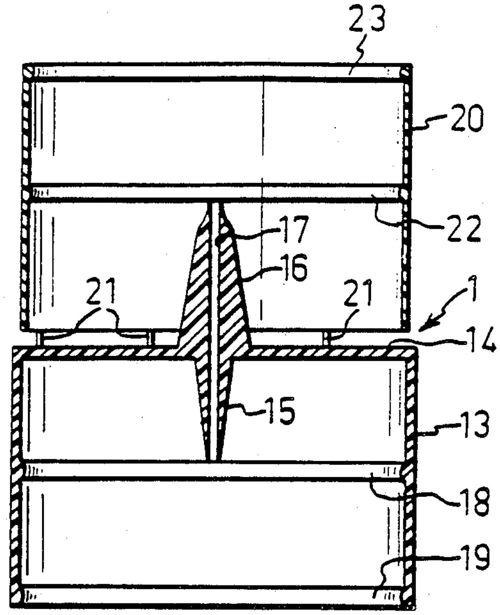
FIG. 3 is a longitudinal section of a connector according to the invention.

The embodiment of the connector 1 as illustrated in FIG. 3, which preferably is made of plastic, comprises a sleeve 13 having an open end and another end closed by means of a partition 14. Extending from the end of the partition 14 toward the open end of the sleeve 13, is a piercing member 15 in the form of a truncated 5 cone. A connecting member 16 extends from the partition 14 in the opposite direction to the piercing member 15. The connecting member 16 is conical along the major part of its length and thus can constitute one part of a so-called luer coupling. A through passage 17 communicates the piercing member 15 with the connecting member 16 and thus extends also through the partition 14. More particularly, the passage 17 opens into the free end of the piercing member 15 and the connecting member 16. A sharp cutting edge is formed around the opening of the passage 17 into the piercing member 15. A similar sharp cutting edge is formed around the opening of the passage 17 into the connecting member 16 which thus also constitutes a piercing member. The sleeve 13 has a first inner bead 18 approximately on a level with the point of the piercing member 15. A second bead 19 is formed at the open end of the sleeve 13.

The connector 1 shown in FIG. 3 furthermore has an extension 20 of the sleeve 13, said extension 20 extending in the same direction as the connecting member 16. Also the extension 20 is sleeve-shaped, although not connected with the sleeve 13 along its entire circumference, but only within limited portions 21. Like the sleeve 13, the extension 20 furthermore has an inner bead 22 approximately on a level with the point of the connecting member 16, as well as a bead 23 at its open outer end.

Figure 4:
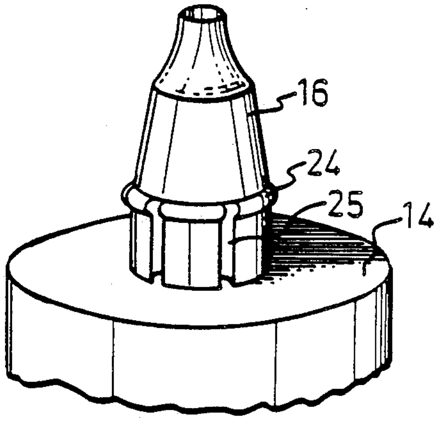
FIG. 4 is a perspective view of the connecting and piercing members of the connector.

FIG. 4 illustrates another embodiment of the connecting member 16. Here, the portion of the connecting member 16 nearest the partition 14 is cylindrical and delimited from the conical portion by a collar 24. Axial grooves 25 extend along the cylindrical portion from the partition 14 and past the collar 24.

Figure 5:
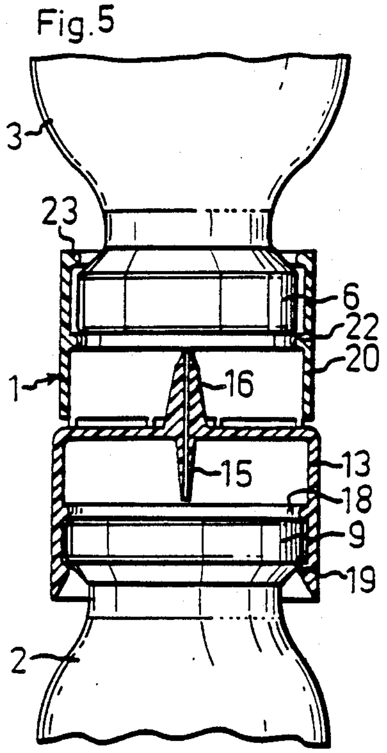
FIGS. 5 and 6 are longitudinal sections illustrating the retracted and inserted positions of the connector according to FIG. 3 relative to the containers according to FIGS. 1 and 2.

In FIG. 5, the connector 1 is in its retracted position relative to both the container 2 and the container 3.

More particularly, the flange 7 of the container 2 is accommodated by the space defined by the inner side of the sleeve 13 and the beads 18 and 19. The container 2 is insertable into this position past the bead 19 because the material of the sleeve 13 is resilient. Similarly, the container 3 and its flange 4 are accommodated by the space which is formed in the extension 20 between the beads 22 and 23. In the positions indicated, the point of the piercing member 15 lies outside the rubber stopper 8 in the neck of the container 2, and the point of the connecting member 16 lies outside the closure 5 in the neck of the container 3.

Figure 6:
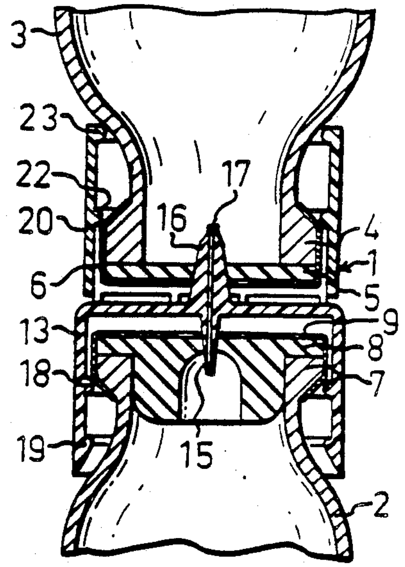

In order to establish communication between the containers 2 and 3 via the passage 17, the containers 2 and 3 are displaced simultaneously or consecutively toward one another into the position shown in FIG. 6, in which the flange 7 lies in the space within the sleeve 13 which is delimited outwardly by the bead 18, and the flange 4 lies in the space in the extension 20 which is delimited outwardly by the bead 22. When the containers 2 and 3 are moved toward one another, their flanges act as plungers in the sleeve 13 and the extension 20, respectively, although a not inconsiderable force is required to effect the movement past the bead 18 and 22, respectively, so that such displacement cannot be made unintentionally. The displacement past the beads 18 and 22 is possible because the connector 1 is made of some suitable resilient material, such as plastic. During the said displacement movement, the piercing member 15 will pierce the closure 8, and the combined connecting and piercing member 16 will pierce the closure 5 so that the containers 2 and 3 will communicate with one another via the passage 17. In this manner, liquid can be transferred from one container to the other. If the connecting member 16 has the shape shown in FIG. 4, the collar 24 will lie, after the displacement, on the inner side of the closure 5, the grooves 25 establishing an air communication into the liquid container 3 to facilitate emptying thereof.

Figure 7:
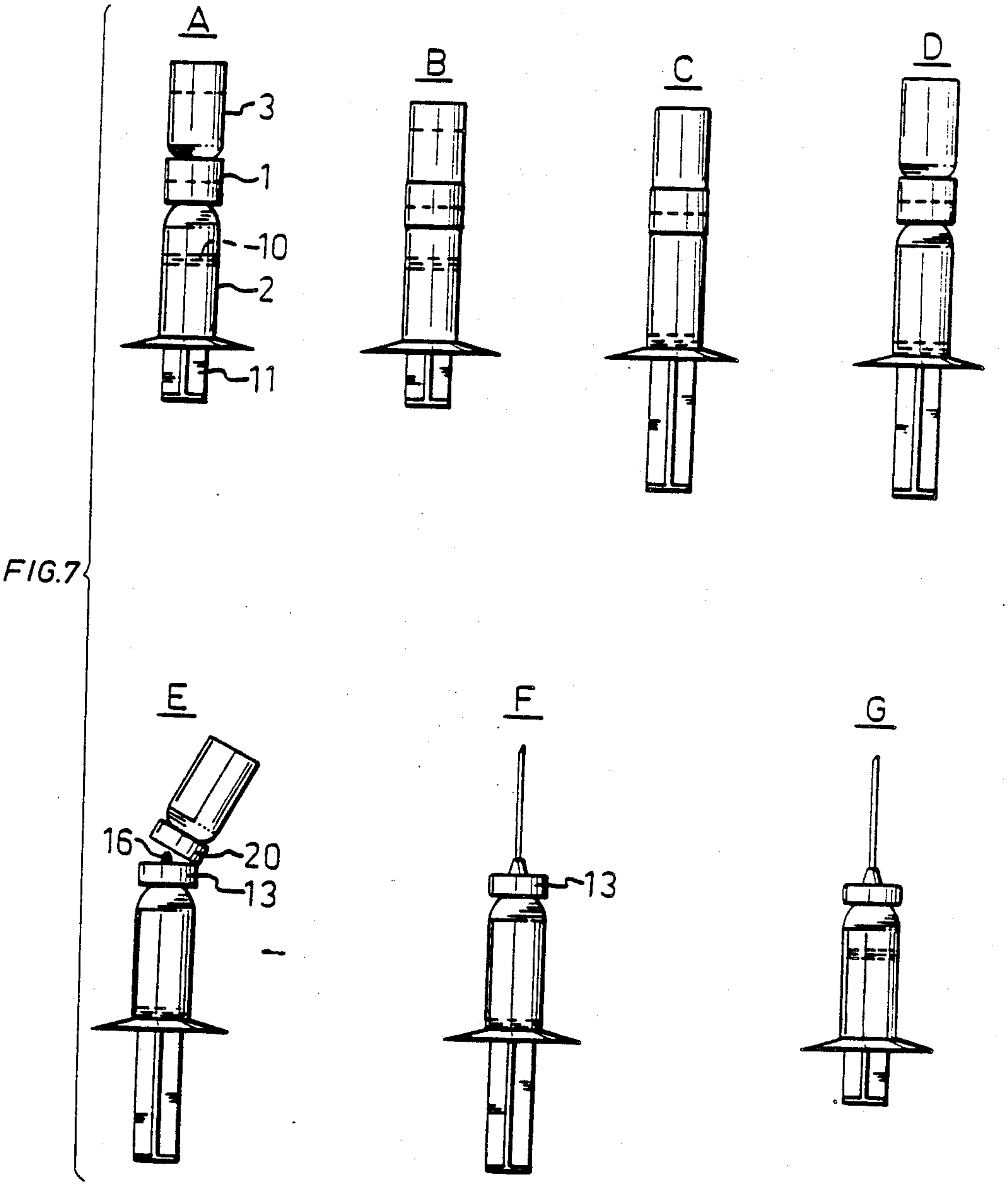
FIG. 7(A–G) illustrates the operating sequence during use of the disposable assembly according to FIG. 1.

All of the steps comprised by an operating sequence during use of the assembly according to FIG. 1 are schematically shown in FIG. 7. In the starting position A, the containers 2 and 3 are in the retracted position relative to the connector 1, as shown also in FIGS. 1 and 5. In the next step B, the containers 2 and 3 are simultaneously or consecutively displaced toward one another, whereby the closures 5 and 8 are pierced and communication is established between the containers 2 and 3, as also shown in FIG. 6. In a subsequent step C, the plunger 10 in the container 2 is retracted, whereby the liquid in the container 2 is transferred by suction to the container 2. In step D, the sleeve 13 then is moved into its retracted position relative to the container 2, whereby the piercing member 15 is retracted from its position piercing the closure 8. In this manner, the drug component and the liquid can be mixed in the container 2 without any risk that the operator is exposed to the mixture since the closure 8 closes itself completely at the point where it has previously been pierced by the piercing member 15. When the mixture within the container 2 is ready for administration, the extension 20 is removed in step E from the sleeve 13 by breaking away the portions 21. Before then, the container 3 has been pushed into its retracted position relative to the extension 20, or been completely removed therefrom.

After the extension 20 has been broken away, the connecting member 16 is exposed to be connected in step F to some suitable means for administration of the mixture in the container 2. This means may be, for example, a cannula, a catheter, a probe, or an infusion device having a connecting member complementary to the connecting member 16. After these connecting members have been connected together, the sleeve 13 is again moved into its inserted position relative to the container 2, as shown in step G of FIG. 7. Administration is then effected by inserting the plunger 10 into the container 2.

Figure 8:
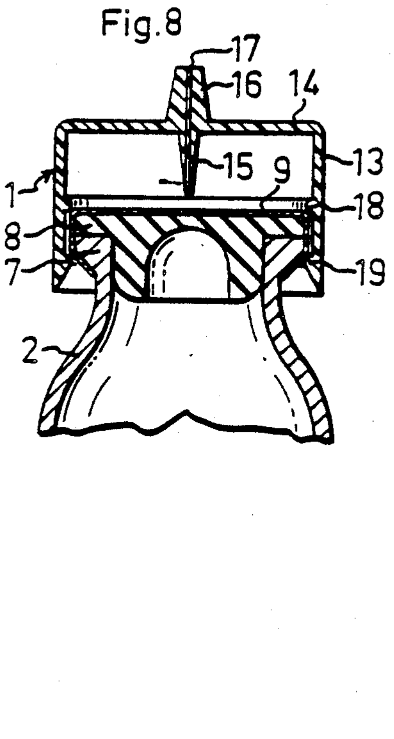
FIGS. 8 and 9 illustrate an alternative connector in, respectively, a retracted and an inserted position relative to a drug container.
Figure 9:
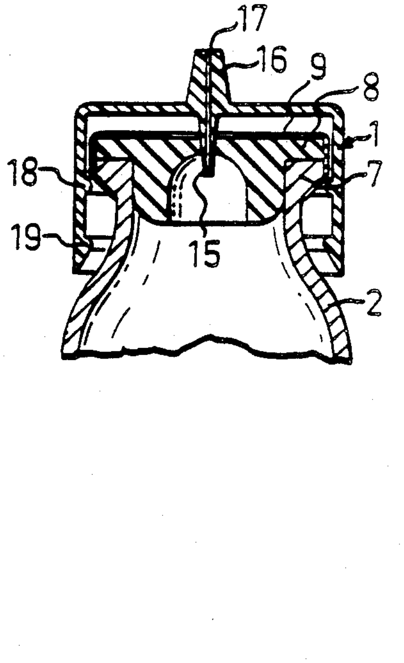

FIGS. 8 and 9 illustrate an alternative embodiment of the connector 1 in which the extension 20 is missing and in which there is no sharp cutting edge for piercing on the connecting member 16. FIG. 8 shows the connector 1 in its retracted position relative to the container 2, and in FIG. 9 the connector is shown in its inserted position relative to the container 2, the piercing member 15 having pierced the closure 8 so that communication is established, via the passage 17, between the container 2 and the free end of the connecting member 16.

Figure 10:
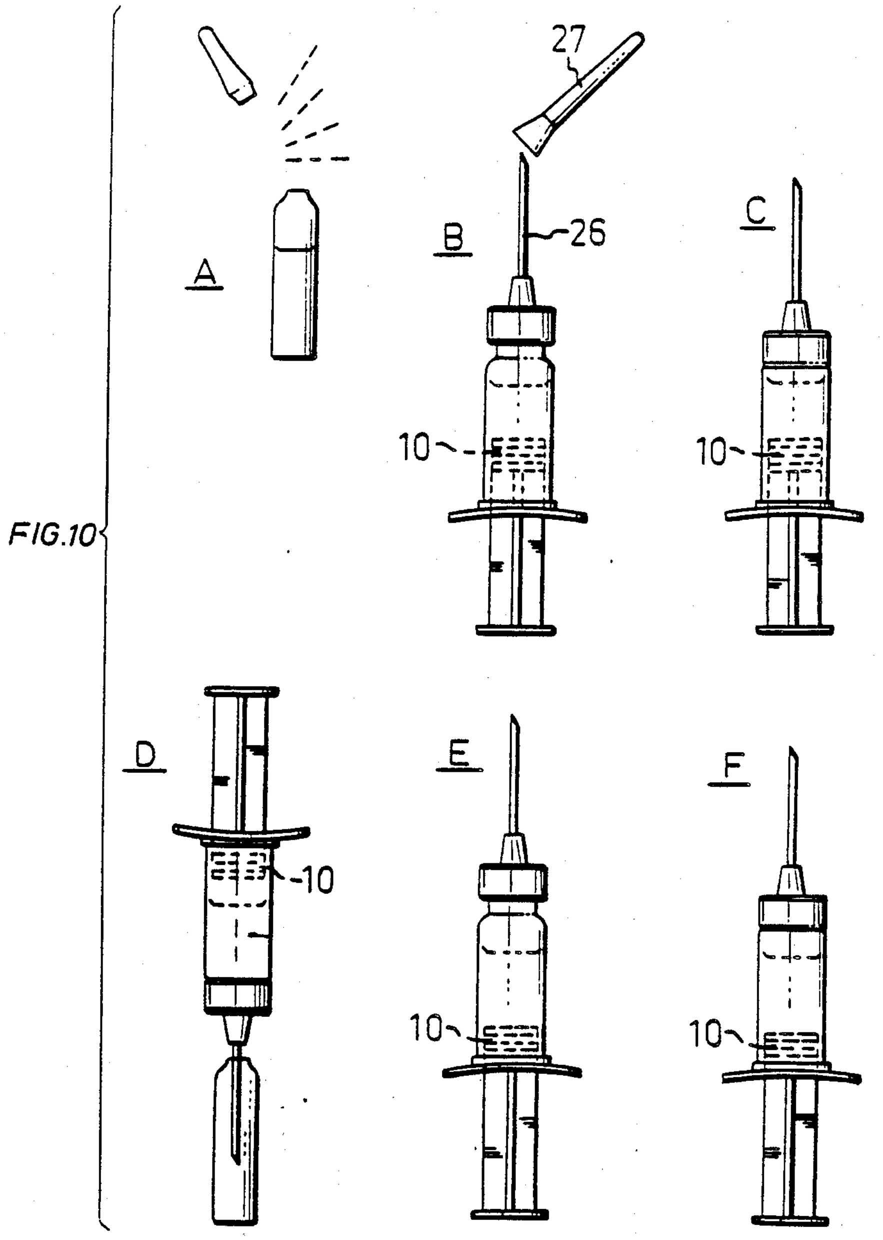
FIG. 10(A–F) illustrates the operating sequence during use of the connector according to FIGS. 8 and 9.

The handling of the connector according to FIGS. 8 and 9 is illustrated in FIG. 10. In a first step A a conventional ampoule containing a predetermined amount of a solvent, is broken. In step B, an external means 26 is attached to the connecting member 16 of the connector. The external means 26 is a cannulla. A needle protector 27 which may be used for protecting the cannula against contamination and physical damage, is also removed. In step C, the connector 1 is moved into the inserted position relative to the container 2, and communication is established between the cannula 26 and the container 2 via the passage 17. In a subsequent step D, solvent is sucked from the ampoule into the drug container 2 by retracting the plunger 10 in the container 2. After that, the container 2 is closed in step E by moving the connector 1 into its retracted position in which the piercing member 15 does nor pierce the closure 8 of the container 2. In position E, a drug in solid form can be left for dissolution. The cannula 26 may also be removed and replaced by some other means for administration. When the device is to be used, the connector 1 is again moved, in step F, from the retracted to the inserted position so that communication is established between the container 2 and the means for administration.

Although the device according to the invention has been described above in its application to dry, cytostatic drugs, a person skilled in the art will appreciate that also other toxic substances, e.g. other drugs which may be in liquid or dry form and which have other pharmacological effects, can be enclosed within the container 2.

Modifications of the embodiments described above are, of course, conceivable. Thus, the beads 19, 22 and 23 can be replaced by other positioning means, while the bead 18 preferably is a continuous bead. Moreover, the extension 20 may serve its function without being sleeve-shaped, and to facilitate its removal from the sleeve 13 it is also possible to reduce the thickness of the material.

Preferred embodiments of the invention have been described above and illustrated in the drawings, but it will be appreciated that these descriptions and drawings merely are intended to illustrate the basic features of the invention and are not intended to restrict the scope of the invention and the appended claims.

I claim:

1. A connecting mechanism adapted to provide fluid communication between first and second containers closed by means of pierceable closure associated with outwardly-directed flange portions, with one of the containers having a plunger means movable within the container, comprising:

(a) a first holding means with first and second end portions, the first end portion end portion being closed and the second end portion being adapted to receive a container with a plunger means associated therewith;

(b) piercing means connected to the closed first end portion of the first holding means, including a first piercing member projecting toward the first holding means and a second piercing member projecting away from the first holding means, the first and second piercing members being in fluid communication with each other;

(c) second holding means connected to the first holding means for holding the other container relative to the second piercing member;

(d) the first and second holding means including positioning means for selectively holding the containers in a retracted position relative to their respective piercing members where the piercing members do not pierce the pierceable closures, and an inserted position where the piercing members pierce the pierceable closures and are in fluid communication with the interior of the containers;

(e) said second piercing member comprising cannula holding means for receiving and holding a cannula in fluid communication with the second piercing member after said other container is removed.

2. A disposable drug-mixing assembly, comprising:

(a) first and second containers, each of which includes a pierceable closure and an outwardly-directed flange portion associated with the pierceable closure, a plunger means moveable within the first container;

(b) a first holding means with first and second end portions, the first end portion being closed and the second end portion being adapted to receive said first container;

(c) piercing means connected to said first end portion including a first piercing member projecting toward said first container and a second piercing member projecting away from said first container, the first and second piercing members being in fluid communication with each other;

(d) second holding means connected to the first holding means for holding said other connector relative to the second piercing member;

(e) the first and second holding means including positioning means for selectively holding their respective containers in a retracted positioned relative to their respective piercing members, where the piercing closures, and an inserted position where the piercing members have pierced the pierceable closures and are in fluid communication with the interior of the containers after movement of the containers from the retracted position toward the inserted position; and (f) said second piercing member comprising cannula holding means for holding a cannula in fluid communication with the second piercing member after said other container is removed.

3. The connecting mechanism of claim 1 or 2, wherein the first holding means includes a sleeve adapted to surround at least the outwardly directed flange portion of the container.

4. The connecting mechanism of claim 1 or 2, wherein the second holding means includes a sleeve adapted to surround at least the outwardly directed flange portion of said other container.

5. The connecting mechanism of claim 1 or 2, and further including connecting means for removably connecting the first and second holding means.

6. The connecting mechanism of claim 5, wherein the first and second holding means includes first and second sleeves, respectively, arranged coaxially with each other and a plurality of breakable connection members for removably connecting the first and second holding means.

7. The connecting mechanism of claim 6, wherein the second sleeve extends beyond the outwardly-directed flange portion of the second container for shielding the pierceable closure from contact by the user when the first and second holding means are disconnected.

8. The connecting mechanism of claim 1 or 2, wherein the second piercing member includes venting means for venting the interior of said other container to the atmosphere when the second piercing mechanism has pierced the pierceable closure thereof.

9. The connecting mechanism of claim 8, wherein the second piercing member includes an elongated member formed of a rigid material with a longitudinal opening and a sharpened end, the venting means including at least one groove formed in the outer surface of elongated member adapted to span the pierceable closure of the container.

10. The connecting mechanism of claim 3, wherein the sleeve includes inwardly-directed flanges spaced apart from each other and slightly smaller than the outwardly-directed flange of the container for holding the container in its retracted position, the inwardly-directed flange being resilient enough so that manual pressure exerted on the container can move it toward its piercing member.

11. The connecting mechanism of claim 4, wherein the sleeve includes inwardly-directed flanges spaced apart from each other and slightly smaller than the outwardly-directed flange of the container for holding the container in its retracted position, the inwardly-directed flange being resilient enough so that manual pressure exerted on the container can move it toward its piercing member.

* * * * *